United States Patent [19]

Naficy

[11] Patent Number: 5,419,759
[45] Date of Patent: May 30, 1995

[54] APPARATUS AND METHODS FOR TREATMENT OF HIV INFECTIONS AND AIDS

[76] Inventor: Sadeque S. Naficy, 12823 Memorial Dr., Houston, Tex. 77024

[21] Appl. No.: 68,510

[22] Filed: May 27, 1993

Related U.S. Application Data

[63] Continuation-in-part of Ser. No. 272,535, Nov. 17, 1988.

[51] Int. Cl.⁶ .............................................. A61M 1/14
[52] U.S. Cl. ......................................... 604/5; 422/44; 210/764; 604/4; 604/6
[58] Field of Search ....................... 604/4-6; 210/764; 422/44-47

[56] References Cited

U.S. PATENT DOCUMENTS

| | | | |
|---|---|---|---|
| 4,381,004 | 4/1983 | Babb | 604/5 |
| 4,787,883 | 11/1988 | Kroyer | 604/4 |
| 4,895,558 | 1/1990 | Cham | 604/4 |
| 4,904,641 | 2/1990 | Eibl et al. | 514/2 |
| 5,039,688 | 8/1991 | Lewis | 604/4 |
| 5,104,373 | 4/1992 | Davidner et al. | 604/5 |
| 5,122,112 | 6/1992 | Jones | 604/5 |

Primary Examiner—Randall L. Green
Assistant Examiner—Rob Clarke
Attorney, Agent, or Firm—Kenneth A. Roddy

[57] ABSTRACT

An extracorporeal apparatus and methods for treatment of HIV (Human Immuno-deficiency Virus) infections and AIDS. Infected blood is drawn from a patient and separated into infected components (comprising plasma, cell-free virus, and infected white cells containing replicating virus) and uninfected components (comprising red cells and platelets). The uninfected components are returned to the patient and the infected components are treated with organic agents. The preferred organic agent is diethyl ether which is used in an amount and over a period of time sufficient to kill the infected cells and the cell-free virus. The preferred apparatus functions at temperatures below 56° C., and includes centrifugal separators for separating the infected components from healthy components; mixers and agitators inside an air-tight chamber void of oxygen where the infected components are mixed and treated with ether; centrifuges and distillators working under vacuum which remove the ether after the completion of treatment; a gas chromatograph with automatic sampling for determining the residues of ether and the safety of the treated components; and mechanisms for returning the treated and safe components, in conjunction with intravenous fluids, separately or together with the healthy components, to the patient. The treatment cycle is repeated until the patient's blood is made free of virus.

28 Claims, 1 Drawing Sheet

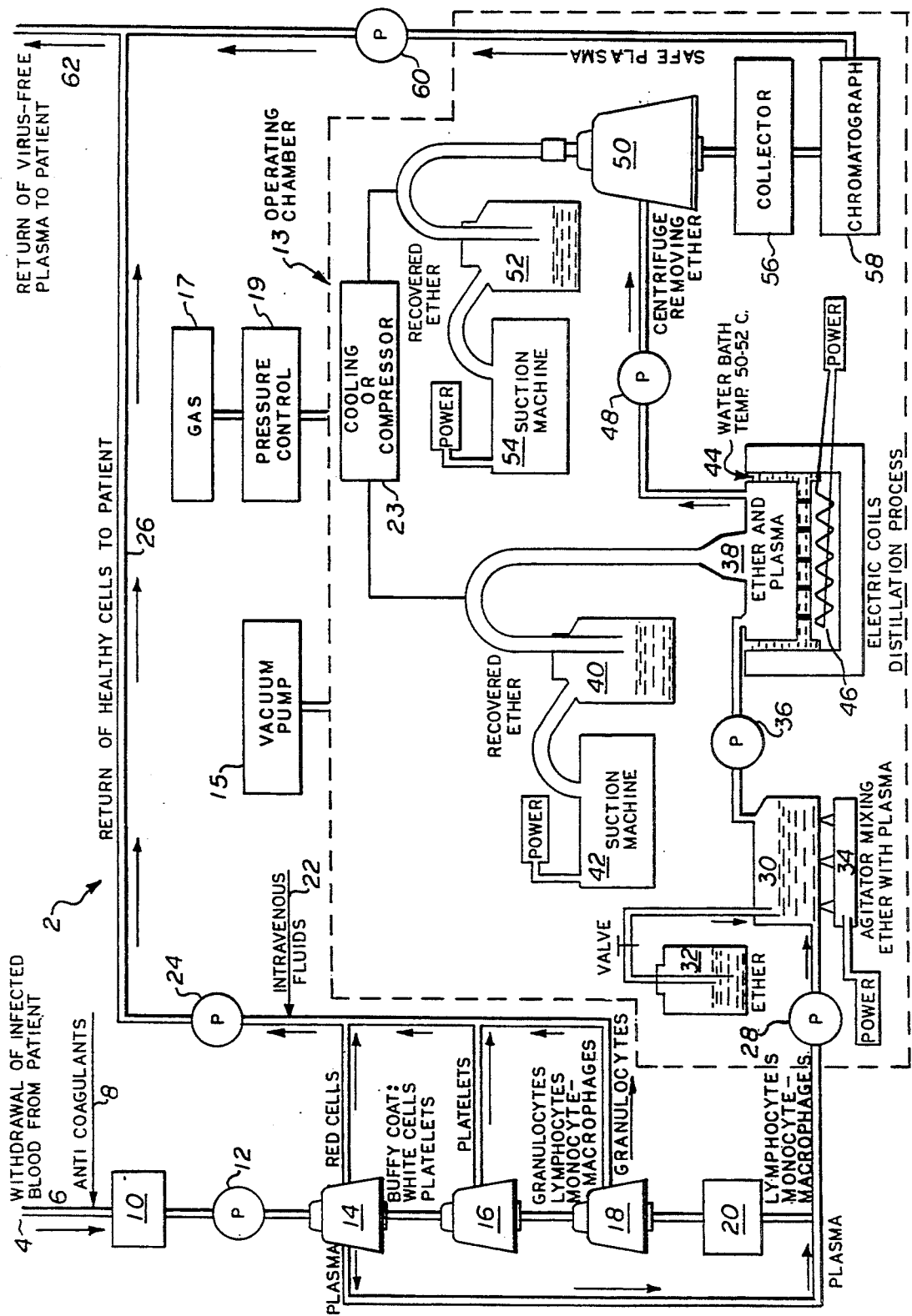

APPARATUS AND METHODS FOR TREATMENT OF HIV INFECTIONS AND AIDS

CROSS REFERENCE TO RELATED APPLICATION

This application is a Continuation-In-Part of U.S. Patent Application Ser. No. 07/272,535 filed Nov. 17, 1988.

FIELD OF THE INVENTION

This invention relates to an extracorporeal apparatus and methods of treatment for infections of blood or plasma caused by the viruses known as enveloped viruses having lipids in their envelope. The apparatus and methods are specifically useful for the treatment of HIV (Human Immunodeficiency Virus) infections, AIDS-related complex, and AID disease.

BACKGROUND OF THE INVENTION

THE EPIDEMIOLOGY OF HIV INFECTIONS: AIDS (Acquired Immuno-deficiency Syndrome) is one of the most deadly diseases which in the recent times has struck humans and has reached epidemic proportions. AIDS has been reported in more than 123 countries.

According to the Center for Disease Control (CDC), the number of HIV-infected individuals in the United States is about 1 to 1.5 million, and the number of cases of full-blown AIDS disease (adults and children) is 242,100. CDC data show that within 7 years 35% of all infected people will progress to full-blown AIDS and another 45% will progress to ARC (AIDS-related complex) or have lymphodenopathy or other signs of immunological disorders. Only 20% will remain asymptomatic, and these too will probably become ill in time. World Health Organization reports the number of HIV infected persons to be about 13 million and the number of people with full-blown AIDS disease to-be-about 2.5 million.

The geographical origin of the HIV infections and AIDS is not exactly known, However, it is believed that the disease came to North America and Europe from Africa. The green monkey in Africa harbors the virus but it seems that he does not develop the disease. Some native Africans use the monkey as pets and for food. It is possible that the virus went through mutations and became patheogenic for man.

The first cases of AIDS were reported in 1981. It emerged as a mysterious syndrome, the etiology of which was unknown. The syndrome for a while inflicted male homosexuals, then it was seen in drug addicts who shared needles, and later it was seen in other risk groups.

THE HUMAN IMMUNODEFICIENCY VIRUS (HIV): Montagnier and his group at the Pasteur Institute of Paris, in 1983 published their work in Science on the discovery of a retrovirus belonging to the family of human T-cell leukemia viruses (HTLV) which had previously been reported. The new retrovirus was isolated from the cervical lymphodenopathy of a patient with Pre-AIDS symptoms. The virus was called LAV (Lymphodenopathy Associated Virus). The virus was a typical type C-RNA tumor virus; it was found to bud from the cell membrane, to prefer magnesium for reverse transcriptase activity, and to have an internal antigen (p. 25) similar to HTLV (p. 24). The virus was transmitted into cord blood lymphocytes and the virus produced by these cells was similar to the original isolate. They concluded that this virus as well as the previous HTLV isolates belonged to a general family of T-lymphotropic retroviruses, and that they might be involved in several pathological syndromes including AIDS.

Gallo and his group at the National Cancer Institute reported their work, also in Science, in 1984 on the isolation of cytopathic retroviruses from 48 patients with AIDS and at risk for AIDS. These retroviruses also appeared to belong to the HTLV family but they differed from them in morphological, biological and immunological characteristics. They concluded that these retroviruses, now called HTLV-III, might be the primary cause of AIDS.

These two independent findings confirmed each other. It was then widely accepted that the etiologic virus of AIDS was the newly discovered retrovirus. The retrovirus has now been called Human Immunodeficiency Virus (HIV).

THE BIOLOGY OF HIV: The virus is an RNA virus and it has the enzyme reverse transcriptase which enables it to make a DNA copy of the viral RNA. The virus has an outer envelope and a dense cylindrical core containing RNA genome. The envelope consists of a lipid membrane with protruding spikes which are coated with glycoproteins. The glycoproteins contain different sugar molecules, some of which appear to be constant, but some may be variable. It is thought that it is the variability of these sugar molecules that eludes the body's immune system in detecting the virus particles. Genes that code for structural components of HIV include the gag gene which codes for core, the env gene which codes for envelope proteins, and the pol gene which encodes viral reverse transcriptase. The gag, pol and env genes are common to all retroviruses. The diameter of the virus is 100–120 nm and it is produced in high numbers from infected cells by budding from the cell membrane in culture.

The virus exists in the blood circulation of the patient in two forms: As cell-free virus or mature virion having a lipid envelope, and as cell-associated virus or replicating virus in the infected cells (T-4 lymphocytes, monocyte-macrophages). The virus is essentially an intracellular parasite and in order to survive and perpetuate itself it has to penetrate and infect the host cells. The lipid envelope with its glycoprotein spikes provide the means for penetrating and infecting the white cells. The virus will replicate inside the infected cells and will produce mature virions with lipid envelope and glycoprotein spikes, budding from the membrane of the infected cell. These mature virions in turn will penetrate and infect the new and healthy cells as they are released from the hematopoietic system, and the vicious cycle will go on.

THE T-4 MOLECULE AND HIV: Laboratory studies of AIDS patients have revealed a depletion of T-4 helper lymphocytes in their peripheral blood. This results in an overall decrease of lymphocytes as well as inversion of T-4 helper lymphocytes to T-8 suppressor lymphocytes. The function of T-4 receptor is not exactly known, but it is known that the receptor associates closely with a type of cell antigen that must be present on an antigen-presenting cell in order for the T-4 lymphocytes to interact with it and recognize a foreign antigen. HIV replicates in T-4+ lymphocytes and apparently not in other types of lymphocytes.

The target host cells invaded by HIV known today include T-4 lymphocytes, monocytes, macrophages and colorectal cells (lymphoid tissues). All of these cells contain messenger RNA for T-4 molecule and express the T-4 protein on the cell surface. The T-4 gene is also expressed on cells distributed throughout the neuraxis. A recent series of experiments has demonstrated that cells that do not normally have the T-4 molecule on their surface and are resistant to HIV infection in vitro become capable of being infected after genetic engineering and expressing the T-4 antigen on their surface. Thus, the T-4 molecule appears to be necessary for HIV infection of human cells.

Other studies showed viral RNA, by in situ hybridization, in the brain tissue. Culture of brain biopsy of a seropositive patient with progressive dementia showed monocytoid cells which by electron microscopy revealed mature virions. Viral RNA was detected in the brain tissues of 2 patients with AIDS encephalopathy. In an infant with Lymphocytic Interstitial Pneumonia, cells were found in the lung tissue to be positive for HTLV-III RNA. It is thought that the infected monocyte-macrophages may carry the virus to these organs.

As to how many years after the patient's exposure to HIV, it will take for the virus to be carried to these organs by the monocyte-macrophages, and as to whether or not the monocyte-macrophages will eventually carry the virus to these organs in every infected patient, is not known. It is also not certain as to whether the virus particles found in these organs are latent or possibly some of these virus particles may be replicating at times, and thereby re-stocking the peripheral blood with mature viruses.

Most persons having antibodies to the virus appear to be infectious, i.e. the virus can be isolated from their peripheral blood lymphocytes. A patient may be infected, i.e. may carry the virus in T-4 lymphocytes and blood, for many years and not be symptomatic.

CLINICAL CRITERIA OF PRE-AIDS AND AIDS: Overt AIDS (Acquired Immuno-deficiency Syndrome) is preceded by a period of prodrome that may last for many months (ARC or AIDS-related complex). The patient develops fever, weight loss, malaise, lymphodenopathy and recurrent chronic diarrhea. The full-blown AIDS is characterized by weight loss, fever, severe headache, neck stiffness, arthralgia and skin rash. The patient develops opportunistic infections including: Pneumocystis carinii pneumonia, cytomegalovirus infections, toxoplasmosis, oral condidiasis, and intestinal cryptococcosis with resultant vitamin $B_{12}$ deficiency. Herpes simplex virus (HSV) infections are common in patients with AIDS and may be severe and persistent requiring intravenous therapy by acyclovir. Other findings include: Gradual gait disturbance, paraplegia, spinal cord degeneration, and chronic dementia.

SUSCEPTIBLE GROUPS: Patients that have been described with AIDS: Homosexual males, intravenous drug users, patients with hemophilia treated with transfusion of blood or blood products, female partners of males with AIDS, infants born of mothers having AIDS. No one is known not to be at risk for AIDS.

LABORATORY STUDIES: A number of laboratory tests have been developed to detect the serum antibodies of HIV antigens. Some of these tests are done at special clinical laboratories and some are mainly used for research.

The immunodeficiency is manifested by skin test anergy and decrease in T-4 helper lymphocytes and inversion of T-helper to T-suppressor ratios in the peripheral blood. Cultures of blood are positive for HIV. If there is involvement of the central nervous system, cultures of cerebrospinal fluid will also be positive for HIV.

Enzyme-linked immunosorbent assays (ELISA) are used to detect antibody to Human Immonodeficiency Virus (HIV) for screening blood products, for clinical purposes and for epidemiologic studies. Confirmation is accomplished by a second assay such as the Western blot test.

In Western blot, HIV antigens are separated electrophoretically and the ELISA-reactive serum is tested against all of these separated antigens. Clear reactivity to certain virus antigens demonstrates true infection with HIV.

Like other serologic tests, the ELISA indicates the occurrence of past infection. However, individuals with confirmed test results are presumed to be currently infected and capable of transmitting infection through blood or sexual contact.

Seroconversion or the presence of detectable antibody levels is seen at 4 to 12 weeks after infection occurs. However, prolonged seronegativity up to a year or even longer has been reported.

INACTIVATION OF HTLV-III/LAV IN LABORATORY SETTING: A number of studies have been recently published on the effects of physical and chemical agents on HTLV-III/LAV. One of these studies showed that the virus titer could be reduced by 1 log (tenfold) at 60° C. for 32 minutes. Another study found that after exposure up to $2.5 \times 10^5$ rad gamma rays the virus was still infectious for human lymphocytes. It should be noted that the amount used for food material is generally at least 10 times lower than this. To inactivate the virus a dose higher than $2.5 \times 10^5$ rad would be needed. It was also found that LAV reverse transcriptase activity was slightly sensitive to UV radiation, the enzyme activity decreasing as a function of the delivered dose. No infectious virus was detected in their infectivity assay in samples irradiated with more than $5 \times 10^5$ J/m$^2$.

Another study found that 1% gluteraldehyde or 25% ethanol is sufficient to disinfect medical instruments. A recent study published in 1987 demonstrated that viral infectivity of HTLV-III/LAV was undetectable and was reduced more than 7 $\log_{10}$ TCIP$_{50}$ within one minute with copious amounts of 0.5% sodium hypochlorite, 70% alcohol, or 0.5% nonidet-P40, and within ten minutes with 0.08% quaternary ammonium chloride or with a 1:1 mixture of acetone-alcohol.

The authors used these results to provide a rational basis to prevent the accidental spread of HTLV-III/LAV in the laboratory or clinical setting. The authors did not consider these tests or the results of these tests to provide a method or means with which the treatment of HTLV-III/LAV infections of a patient could be effected.

BRIEF DESCRIPTION OF THE PRIOR ART

EFFECTS OF ANTIVIRAL AGENTS ON AIDS VIRUS (HIV): Antibiotics are not effective on viruses. Prior art does not offer a drug or a method to kill the AIDS virus. Prior art uses mainly nucleoside analogues, e.g. zidovudine or ribavirin, to treat HIV infections and AIDS. However, these antiviral drugs have been found to be effective only to a limited extent. These drugs are virustatic and not virucidal; they can inhibit the viral replication but they can not kill the virus.

Azidothymidine (zidovudine) has recently been approved by the FDA for some years now, and it has been offered in the market under the trade name of Retrovir. Zidovudine is a thymidine analogue; it is phosphorylated by cellular kinases to zidovudine triphosphate. The viral-enzyme reverse transcriptase incorporates zidovudine triphosphate (which competes with thymidine triphosphate) into viral DNA. Once incorporated into viral DNA, zidovudine triphosphate prematurely terminates the viral DNA, thus it inhibits the viral replication.

Ribavirin, which is another nucleoside analogue, can inhibit the viral replication by a similar mechanism. It has been reported that ribavirin delays the onset of AIDS in patients with lymphodenopathy.

A study sponsored by the National Institute of Allergy and Infectious Diseases, is now underway on seropositive patients who do not have AIDS or AIDS-related complex. The study is a two-pronged treatment combining the antiviral zidovudine and the immune-boosting agent interleukin-2.

Clinical trials which were the basis of approval of zidovudine have demonstrated that opportunistic infections and deaths were lower in the Retrovir group than the placebo group; T-4 cells were also higher in the Retrovir group.

Since it has been recognized that AIDS is an infection of the immune system the attention of the prior art has been focused on the search for therapies in two general areas: a) drugs with direct antiviral effects on the etiologic organism, b) immunomodulators that could restore the immune system. It is important to know that antiviral drugs, used by prior art, are not likely to restore the immunological function directly and immunomodulators are not likely to exert a direct effect on the virus.

The identification of the T-4 molecule as the receptor for the virus suggests that it may be possible to inhibit viral replication by interfering with the attachment of the virus to susceptible host cells. Monoclonal antibodies specific for T-4 receptor have been proposed by the prior art for this purpose.

The use of bone marrow grafts has been studied by prior art in identical twins, one of whom having AIDS. In three such pairs studied, only in one individual was the immune function restored after viral levels were reduced.

THE PROBLEMS WITH PRIOR ART: There has been a number of complications reported to be associated with Retrovir therapy including nausea, myalgia, insomnia and severe headaches. However, the most serious and life threatening complications are hematologic toxicity including severe anemia and granulocytopenia requiring repeated blood transfusions and/or interruption of therapy. Another complication is hepatotoxicity. So much so that Burroughs Wellcome Co., the manufacturer of Retrovir, is now printing the following warning in its publication of the drug:

WARNING: Therapy with Retrovir (zidovudine) is often associated with hematologic toxicity including granulocytepenia and severe anemia requiring transfusions. In addition, patients treated with zidovudine may continue to develop opportunistic infections and other complications of AIDS and AIDS-related complex (ARC) caused by the immunodeficiency virus (HIV). The safety and efficacy of zidovudine have been established only for certain adult AIDS and advanced ARC patients.

The main disappointment with zidovudine, in addition to the hematologic toxicity, has been that it has failed to re-establish or at least improve the status of the immune system which is shattered in AIDS and ARC patients.

In the inventor's opinion this problem is inherent not only in the nucleoside analogues but in any antiviral drug or any method of treatment which may only be able to inhibit the viral replication in cell-associated virus, and which is not able to kill the cell-free virus. The cell-free virus which is thus not killed keeps penetrating and infecting the fresh and uninfected nucleated blood cells, i.e. T-4 lymphocytes, monocytes and macrophages, as they are released from the hematopoietic system. On the other hand, probably zidovudine somehow does not reach or does not inhibit all the replicating viruses inside the infected cells. Consequently, these replicating viruses produce mature virions which are released in the blood and which will in turn infect the fresh T-4 lymphocytes. Thus, the vicious cycle will perpetuate itself and the patient will continue to have low T-4 lymphocytes, will continue to have immunodeficiency, and will continue to be prone to the opportunistic infections. Eventually the patient will die, only it may take longer.

Another problem with prior art is the emergence of drug-resistant viral mutants. Toxic effects of the antiviral drugs on host cells is also a problem since viral replication is an intracellular process.

DESCRIPTION OF THE INVENTION

EXTRACORPOREAL METHOD OF TREATMENT: The extracorporeal method for administering various treatments is known to the art. So the extracorporeal method of treatment per se is not claimed. What is novel and it is claimed in the instant invention is the apparatus and methods in which organic agents and preferably highly volatile organic agents are used extracorporeally under special conditions to treat the infections of blood or plasma caused by enveloped viruses, specifically HIV (Human Immunodeficiency Virus) or AIDS virus.

Kidney dialysis is one of the oldest methods in which a patient's blood is externally treated. In a patient with kidney insufficiency whose blood accumulates high levels of creatinine, urea and other materials, the blood is directed outside of the body into a dialysis machine wherein the blood is purified by means of certain membranes and the purified blood is then returned to the patient.

Pump oxygenator is another form of device in which a patient's blood is externally processed and oxygenated while surgical procedures are being performed on the heart.

In U.S. Pat. No. 4,321,919; 4,398,906; 4,429,744; and 4,464,166, issued to Edelson, the external treatment methods for diseases in which there is a pathological increase of lymphocytes, such as cutaneous T-cell lymphoma, have been discussed. In these methods the patient's blood in the presence of a chemical or an antibody is irradiated with ultraviolet light. Ultraviolet light effects a bonding between the lymphocytes and the chemical or antibody thus inhibiting the metabolic processes of the lymphocytes.

In the U.S. Pat. No. 4,381,004 titled EXTRACORPOREAL SYSTEMS FOR TREATMENT OF IN- FECTIONS AND PARASITIC DISEASES, a method for treatment for viral diseases in general has been provided. However, that method of prior art has a major problem: it uses antiviral drugs for treatment of viral infections in blood or plasma. Whereas it is well known to the art that antiviral drugs have no effects whatsoever on the mature viruses or virions (cell-free viruses). As it has been mentioned in THE PROBLEMS WITH PRIOR ART, the effects of antiviral drugs are only on the replicating viruses inside the infected cells. Thus, by using this method of the prior art the cell-free virus or virion which is not affected by the antiviral drugs will keep penetrating and infecting the fresh white blood cells, particularly the T-4 helper lymphocytes. Consequently, the biological cycle of the virus will still go on. In other words, as I have explained before, it is the inherent limitation of the effects of the antiviral drugs used in prior art which is the problem, regardless of whether these drugs are administered to the patient directly or used extracorporeally. Further, this problem is not dose related, so using antiviral drugs extracorporeally in the hope that larger amounts may give better results would be futile.

MECHANISM OF FUNCTION OF THE INVENTION: As it was noted in the BACKGROUND OF THE INVENTION, The Human Immunodeficiency virus (HIV) exists in the patient's blood circulation in two forms: As cell-associated virus or replicating virus in the infected cells (T-4 lymphocytes and monocyte-macrophages), and as cell-free virus or mature virion having a lipid envelope, in the plasma. These are two different stages of development in which the virus has different biological characteristics.

The present invention consists of an apparatus and methods with which a two-pronged attack is launched, in an extracorporeal setting, against both of these biological forms of the virus existing in the blood or plasma.

The premise of the invention is that in order to break the vicious cycle by which the virus perpetuates itself, it is imperative that we do two things: a) Kill the cell-free virus, b) Stop or substantially reduce the replication of virus inside the infected cells (T-4 lymphocytes and monocyte-macrophages), by killing these cells or removing them from the blood. The virus is essentially an intracellular parasite and in order to survive and perpetuate itself it has to penetrate and get inside the host white cells (particularly T-4 lymphocytes). If the cell-free virus is allowed to go on penetrating and infecting the fresh white cells as these are produced and released by the hematopoietic system, the vicious cycle will not be broken.

KILLING THE CELL-FREE VIRUS AND REPLICATING VIRUS: As it has been described in THE BIOLOGY OF HIV, the AIDS virus (HIV) is an enveloped virus having lipids in its outer envelope. It is this outer envelope with its glycoprotein spikes which provides the means for penetrating and infecting the healthy T-4 lymphocytes, monocytes and macrophages. Since organic solvents, particularly highly volatile ethers, such as diethyl ether and ethyl vinyl ether, alcohols, such as ethyl alcohol and isopropyl alcohol, volatile chlorinated hydrocarbons, such as methylene dichloride and chloroform, can dissolve lipids, I sought to develop a clinical method which would be technically feasible to dissolve or destroy the lipid envelope of HIV by adding diethyl ether to the patient's blood containing cell-free virus; thereby destroying the glycoprotein spikes and rendering the virus unable to penetrate and infect the healthy cells.

However, it was not known as to what would be the effects of the organic solvents such as ether: a) on the blood factors, enzymes, complement, antibodies, etc. that the patient either naturally possesses or has acquired during his life-time and which are vital to the physiological well-being of the patient; b) on the healthy cellular elements such as platelets which are needed for blood coagulation, without which after surgical incisions or injuries the patient may bleed excessively or possibly may bleed to death; c) on the red cells which are needed for blood oxygenation transporting the oxygenated blood to the various organs; d) on the granulocytes which are needed for defense against offensive micro-organisms; and e) on the replicating virus inside the infected T-4 lymphocytes, monocytes and macrophages.

To elucidate these points, three series of experiments were conducted:

I. To study the effects of ether on the complement, enzymes, antibodies, blood factors, etc., various amounts of ether were added to human plasma or serum in the test tubes (from 10% to 50% by volume), The mixture was incubated for varying periods of time (from 5 minutes to 30 minutes) at room temperature (22°±20°). After incubation, the ether was removed by placing the test tubes in a water bath at temperatures below 56° C. (complement and some other components of plasma get destroyed at 56° C. or higher temperatures). The test tubes were then sent to a reliable Clinical Laboratory for testing. Recommended test for evaluation of the immune system, serum antibodies, various proteins and ,enzymes were requested. The results were compared with the results from base-line tests without adding ether. All the tests showed values within the normal range indicating that ether did not damage or destroy complement, enzymes, antibodies, blood factors, etc.

The studies on the effects of ether on HIV and on the white cells infected with HIV were done at Bionetics Research, Inc., Kensington Md.

II. The first pilot study was done to determine the concentration of ether needed to kill the cell-free virus in plasma. In this first study we ran into a problem but we also discovered that low concentrations of ether would also kill the living cells. After exposing the cell-free virus to varying dilutions of ether and after incubationg the test tubes over varying amounts of time, then removing the ether, apparently there had been a residual amount of ether which had not been removed. After the first week we found that this residual ether had been toxic to the Target Cells (H-9 lymphocytes), leaving no viable Target Cells to which the virus could be transmitted (if there were any viruses that had survived the exposure to ether). Consequently the cultures related to all the dilutions of ether showed no viral growth. It was not clear as to whether the negative growth could be attributed to the effect of ether on the virus, or to the death of the cells.

We repeated the study with an improvement in the technique. To make certain that there was no residual ether in the culture medium, after exposure of virus to ether and incubation, the test tubes were centrifuged. The virus pellet was thus separated and resuspended in culture medium with Target Cells.

In this study two groups of tubes containing 3-4 logs/ml of virus were tested. One group was exposed to from 5% to 50% of ether by volume and incubated at room temperature for 5 minutes, the second group was exposed to the same graduated amounts of ether and incubated for 10 minutes.

After 4 weeks, the positive culture tubes (virus unexposed to ether) showed growth of virus but all test tubes containing plasma spiked with HIV-I and exposed to ether showed negative growth indicating that no infectious virus could be recovered after incubation of HIV-I spiked plasma with as little as 5% diethyl ether (V/V) for 5 minutes at room temperature (22°±2°).

We repeated the study at a larger scale. This time we spiked the plasma with HIV-I to contain 7 $\log_{10}$ $TCID_{50}$/ml HIV-I. The results went beyond those of the first study and showed that up to 7 logs of virus could be inactivated by exposure to 5% ether for 5 minutes.

III. Having discovered that H-9 lymphocytes could be killed by low concentrations of ether, I decided to determine the lowest concentration of ether and exposure-time needed to kill the infected H-9 lymphocytes. We then conducted a third study exposing HIV-I/infected H-9 lymphocytes to graduated amounts of ether (5%, 10%, 15% and 20%) incubating them for 5 minutes or 10 minutes. Incubation of HIV-I/H-9 infected cells with 10% or greater (V/V) diethyl ether for 5 or 10 minutes at 22°±2°inactivated all infectious virus. The HIV-I/H-9 infected cells treated with diethyl ether were not able to infect additional target cells when co-cultivated with equal numbers of H-9 cells.

In summary my studies demonstrated the following:
a) No infectious virus could be recovered after 4 weeks from infected plasma containing up to 7 logs of HIV-I exposed to 5% ether at room temperature for 5 minutes.
b) No infectious virus could be recovered after 4 weeks from HIV-I/infected H-9 lymphocytes at a concentration of $0.5 \times 10^6$/ml exposed to 10% ether for 5 minutes at room temperature.
c) Living H-9 lymphocytes could be killed by exposing them to low concentrations of ether, 10% for 5 minutes, at room temperature.
d) Ether in concentrations up to 50% will not damage or destroy the antibodies, complement, blood factors, enzymes, etc. present in the plasma.
e) Ether will kill the living blood cells, in the concentrations necessary to kill the virus.

From these studies it becomes clear that there would be a prohibitive problem in the use of ether if it were to be injected directly in the blood (intravenously) to effect the proposed treatment. It should be pointed out that ether was used for decades, and it may still be used in some parts of the world, in small amounts for general anesthesia and it has always been recognized as being the safest anesthetic agent. However, if based on the kilograms of body weight or based on the blood volume, sufficient amounts of ether are administered to produce the therapeutic concentration of 10% by volume in the plasma in order to kill both the cell-free virus and the infected cells containing replicating virus, the same concentration would also kill all the healthy cellular elements which are vital to the patient (red cells, granulocytes, platelets). This of course is not compatible with life; because total loss of all red cells will cause immediate cessation of oxygenation; and total loss of platelets will dangerously jeopardize the clotting mechanism. Another problem would be that the volume of ether administered at one time to attain such concentration would also be incompatible with life because of its effects on the central nervous system.

The only way to accomplish the idea using organic solvents, such as diethyl ether for treatment of HIV infections, is to treat the infected blood in an extracorporeal apparatus. In accordance with the apparatus and methods of the present invention, the healthy cellular elements (red cells, platelets, and also granulocytes, if need be) are first removed from the infected blood and returned to the patient. Then the infected plasma containing cell-free virus and replicating virus inside the infected cells is mixed and treated with sufficient amounts of organic solvent, viz., diethyl ether, (about 10% or more). The mixture is agitated at room temperature in order to prevent the ether from getting separated from plasma because of its volatility. After the treatment is completed, the ether is removed and the treated plasma is returned to the patient. Diethyl ether is highly volatile and it has a boiling point of only 34.431° C. Removal of ether from treated plasma is accomplished by distillation below 56° C. under vacuum or by centrifugal forces under vacuum. To make certain that no residual ether is remaining in the treated plasma, a combination of the two techniques may be used. Other methods for removal of the organic solvents from the plasma after the completion of treatment are neutralizing or denaturing the organic solvents, thereby rendering the treated plasma safe to be returned to the patient.

Other forms of ether useful in the present invention are: methyl ether, ethyl vinyl ether, and propyl ether. Halogenated ethers that are currently used as general anesthetic agents can also be used, including: methoxyflurane (2,2-dichloro-1,1-difluoroethyl methyl ether, Penthrane); enflurane (2-chloro-1,1,2-trifluoroethyl difluoromethyl ether, Ethrane); isoflurane (1-chloro-2,2,2-trifluoroethyl difluoromethyl ether, Forane); and fluroxene (2,2,2-trifflfluoroethyl vinyl ether).

Another group of organic agents that could be used to achieve the goal of this invention is halogenated hydrocarbons including: halothane (2-bromo-2-chloro-1,1,1-trifluoroethane, Fluothane), which is also a general anesthetic; trichloroethylene; dichloromethane (methylene chloride); ethyl chloride; ethylene; 1,1,1-trichloroethane; and xylene (dimethyl benzene).

The group of alcohols which is also useful for this invention includes ethyl alcohol and isopropyl alcohol. Lastly, chloroform and acetone could be used.

The treatment apparatus is operated either continuously or in cycles. Therefore, the flow of infected blood from the patient to the apparatus and the flow of treated blood from the apparatus back to the patient may be continuous or intermittent. In any case the treatment is continued until the entire blood is made substantially free from viable cell-free virus and from viable infected white cells containing replicating virus.

When the initial treatment or treatments have reached a point when the viable infected white cells have been substantially eliminated from the blood circulations as indicated by blood tests, from then on it would not be necessary to include the white cells in the plasma to be treated by organic solvents. At that point the infected plasma is separated from all the blood cells and the infected plasma containing cell-free virus is treated by organic solvents, preferably ether. This modification of technique is advantageous because after the initial treatments when the infected white cells in the blood have been killed and the fresh and healthy T-4 lymphocytes and monocytemacrophage have entered the blood circulation from the hematopoietic system, it is desirable to preserve these healthy cells and not subject them to the effects of ether any more. The T-4 helper lymphocytes play an important role in maintaining the patient's immune system. One of the main reasons why the immune system of the AIDS patient becomes weak and the patient becomes prone to opportunistic infections such as pneumocystic carinii pneumonia, etc., is that the patient keeps losing his healthy T-4 helper lymphocytes.

As it was mentioned above, my laboratory studies showed that the minimum amounts of organic agent (e.g. ether) applied over the shortest period of time needed to effect the treatment, i.e., to kill the infected cells, and to inactivate the cell-free virus, will also kill the healthy cellular elements, i.e., the red cells and platelets; which are necessary for continuation of life of the patient., Therefore, it is imperative that these healthy cells be separated, preserved, and returned to the patient. Only the infected components should be exposed and treated with organic agents.

In other words, I have established that treating the whole blood with amounts of organic agents over periods of time needed to kill the infected cells is not compatible with the physiological well being of the patient; therefore, the whole blood should not be treated.

The specific type of equipment used to accomplish component separation and treatment will make no difference, as long as the equipment used and the procedure followed are in accordance with the present invention. What is currently used in the field of blood component separation, are a variety of centrifugal separators, or as they are called in the industry, cell separators. Filtration systems are also used in conjunction with cell separators to filter cells from platelets, or to filter the types of white cells from each other.

The number and location of the cell separators, filters, and the types and locations of other pieces of equipment shown in the drawings, and discussed in the DESCRIPTION OF THE PREFERRED EMBODIMENT, illustrate the concept that: (a) necessary pieces of equipment are used to separate the infected components of blood; (b) these components are then treated with certain amounts of organic agents over given periods of time, then appropriate equipment are utilized to remove the organic agent from the treated components, and after removal; (c) the treated components are tested to determine their safety, by measuring the residues of organic agents, and thereafter, (d) if the residues are acceptable, the treated components are returned to the patient.

It should be understood that those who are experienced in the design and construction of this type of apparatus, will select the most suitable materials of construction, and most efficient pieces of equipment available. It should also be understood that additions, modifications, improvements, simplifications, and changes may be made; including changes in the placement of various pieces of equipment in the operating chamber and in the housing, giving consideration to the safety, efficiency, and easiness of operating the apparatus. For example, electronic equipment, computers, circuit boards, microprocessors, controls, relays, special wiring, switches, etc. may be added. Other additions such as disposable units, containers, reservoirs, etc.; or exclusion of certain things which may not be safe to use, or which may not be efficient, or may be too bulky or cumbersome, etc., may be made.

BRIEF DESCRIPTION OF THE DRAWINGS

FIG. 1 is the sole drawing illustrating schematically the basic components of the extracorporeal apparatus used for treatment of HIV infections and AIDS, according to the method of the present invention.

DESCRIPTION OF THE PREFERRED EMBODIMENT

There is shown in FIG. 1 a schematic drawing of an apparatus 2 operating in accordance with the present invention. With the exception of the components 30, 32 and 34 for adding ether and agitating and mixing ether with infected plasma; and also components 38, 40, 42, 44 and 46 for separating the ether from plasma by distillation process at temperatures 50°–52° C., the bulk of the components of apparatus 2, per se, are commercially available, therefore, the details of their construction will not be given here.

It is demonstrated in FIG. 1 that infected blood is drawn from the patient 4 via the intravenous tubing 6. Typically the withdrawal of blood is done via a needle or catheter inserted in the right antecubital vein. In the preferred embodiment, the flow of blood at withdrawal from the patient 4 into the apparatus and the return of the treated blood from the apparatus back to the patient 58 is continuous. The return of the treated blood is also accomplished by the use of a needle or catheter inserted into the left antecubital vein. The rate of blood flow may be effected by pump 12. Several kinds of such pumps are commercially available.

The preferred embodiment of the apparatus comprises an enclosed, air tight, operating chamber 13 (represented in dashed lines) where the actual treatment of the infected plasma and infected cells is carried out. The operating chamber 13 and other related equipment may be disposed in a housing (not shown).

Since diethyl ether is inflammable and in the presence of sparks, there could be the danger of an explosion, the present invention takes precaution and conducts the treatment with ether and with other inflammable organic agents, in the enclosed, air tight operating chamber 13, in complete absence of oxygen. Before each treatment session, a pump 15 connected with the chamber 13 evacuates all the air from within the chamber. The chamber 13 is then filled with a non-flammable, non-combustible gas 17, such as nitrogen. A gauge and control mechanism 19 maintain the pressure of nitrogen within the chamber 13 considerably higher than the atmospheric pressure (e.g., at 2 or 3 atmospheric pressure) to prevent any potential air leak from outside into the chamber. In this manner, even if there is a spark created by one of the mechanical or electrical components of the apparatus, the spark could not ignite the ether because of the total lack of oxygen.

Anticoagulants are preferably injected into the extracorporeal blood stream at 8 near the point where blood is withdrawn from the patient. The most common anticoagulants are: Trisodium citrate, Sequestrene (EDTA), and heparin.

An occluded vein sensor 10 is preferably used in the path of the blood flow to prevent the formation or continued existence of bubbles in the blood stream. Pump 12 propels the infected blood into centrifuge 14 which separates the red cells and white cells from plasma. The centrifuges 16, 18 and filtration system 20 separate the healthy cellular elements (granulocytes and platelets) from the infected cells (lymphocytes and monocyte-macrophages). Intravenous fluids are added at 22 to these healthy cells (red cells, granulocytes, and platelets), and pump 24 returns them to the patient via the tubing 26. The infected plasma containing cell-free virus and the infected cells containing replicating virus are propelled by pump 28 into mixer 30 where they are mixed with organic solvent preferably ether coming from container 32. The agitator 34 mixes the ether with plasma and infected cells and will not allow ether to get separated from plasma because of its volatility. After treatment is effected, the mixture of treated plasma, lymphocytes, monocyte-macrophages and ether is propelled by pump 36 into the distillation station 38 where the mixture is heated inside water bath 44 to temperatures of 50°–52° C. by electric coils 46. The suction machine 42 aspirates the ether and collects it in container 40. The mixture of plasma and cells still containing some residual ether is propelled by pump 48 into centrifuge 50 where suction machine 54 removes the residual ether separated by centrifuge 50 from plasma and collects it in container 52. The treated plasma is collected in collector 56.

A gas chromatograph 58 equipped with automatic sampling mechanism, takes repeated samples at regular intervals, from the contents of the collector 56 after treatment has been effected, and determines the residues of ether or any other organic agent used, in parts per million or parts per billion depending on the agent used. This is to ensure that the residues of agents used are within the acceptable range, and that the treated plasma or treated cells are safe to be returned to the patient. Pump 60 returns the treated plasma with killed cell-free virus and killed infected cells, to the patient at 62.

After treatment is effected, in the process of removal of ether by centrifuge-vacuum systems and/or distillation systems, cooling mechanisms or compressors 23 are used to compress the vapors of ether, which is then collected in bottles.

It should be pointed out that although the preferred embodiment has been described as a continuous operation and continuous blood flow, the treatment of blood infections caused by enveloped viruses according to the instant invention may also be accomplished by batched technique. This technique is particularly useful in blood banks to treat the units of blood, plasma or blood products before releasing them for transfusion. The technique will prevent the transmission of diseases caused by enveloped viruses from blood donors to transfusion recipients, e.g. hepatitis type B.

As it was pointed out in the DESCRIPTION OF THE INVENTION, during the course of treatment when a point is reached when all the infected lymphocytes and monocytemacrophages have been eliminated from the blood circulation, as indicated by blood tests, from then on it would not be necessary to include the white cells in the plasma to be treated by organic solvents. At that point after centrifuge 14 has separated the blood cells from plasma, the blood cells will all be returned to the patient with the aid of intravenous fluids 22 and pump 24 via line 26; and the centrifuges 16, 18 and filtration system 20 will be bypassed.

While this invention has been described fully and completely with special emphasis upon a preferred embodiment it should be understood that within the scope of the appended claims the invention may be practiced otherwise than as specifically described herein.

I claim:

1. An apparatus for extracorporeal treatment of viral infections of blood of a patient, including HIV (Human Immunodeficiency Virus) infections and AIDS, caused by enveloped viruses having a lipid envelope and spikes covered by glycoproteins, said device comprising the following elements operatively connected with each other:
   (a) a mechanism for withdrawing infected blood from said patient;
   (b) a mechanism connected with said mechanism for withdrawing infected blood for introducing anticoagulants to said infected blood;
   (c) component separators connected with said mechanism for withdrawing infected blood for separating said infected blood substantially into infected components including plasma and white cells, and substantially healthy or un-infected components including red cells and platelets;
   (d) a first return mechanism connected with said component separators for returning said red cells and platelets to said patient;
   (e) at least one reservoir containing organic agents in liquid form selected from the group consisting of ethers, halogenated ethers, halogenated hydrocarbons, chlorinated hydrocarbons, chloroform, and acetone;
   (f) a mixing mechanism connected with said component separators and with said at least one reservoir for mixing and treating said infected components with said organic agents;
   said mixing mechanism mixing and treating said infected components with said organic agents in an amount and over a period of time sufficient to dissolve the envelope and destroy the glycoprotein covered spikes of said viruses (cell-free virus) thereby depriving said viruses of means for penetrating and infecting healthy cells, thus inactivating said enveloped viruses, or sufficient to kill the infected white cells containing virus (replicating virus) thereby stopping the maturation of the virus within said infected white cells without damaging the biochemical constituents of plasma including antibodies, complement, clotting factors, enzymes, and blood factors; said organic agents being otherwise proportionately too harmful to be administered directly to said patient in effective or therapeutic amounts calculated based on the kilograms of body weight or based on the volume of blood;
   (g) a removal mechanism connected with said mixing mechanism for substantially removing, denaturing, or neutralizing said organic agents after the completion of said treatment;
   (h) a measuring mechanism connected with said removal mechanism for measuring the residues of said organic agents in said treated components, after removal of said organic agents, to determine whether said residues are within an acceptable safe range and said treated components are safe for reuse;
   (i) a second return mechanism connected with said measuring mechanism for returning said treated plasma and white cells, separately or in combination, to said patient or a different patient;
   (j) mechanisms connected with said mixing mechanism for introducing suitable fluids into said components, as needed at various points, throughout the cycle of treatment; and (k) mechanisms connected with said first and second return mechanisms and said mixing mechanism for propelling said components, as needed at various points, during the course of treatment.

2. An apparatus according to claim 1 including
an enclosed operating chamber enclosing at least said mixing mechanism in which said treatment is conducted.

3. An apparatus according to claim 2 in which
said operating chamber is air tight and is void of oxygen.

4. An apparatus according to claim 3 in which
said operating chamber is filled with a noncombustible, non-flammable gas.

5. An apparatus according to claim 4 in which
said non-combustible, non-flammable gas has a pressure at least equal to the atmospheric pressure.

6. An apparatus according to claim 4 in which
said non-combustible, non-flammable gas is nitrogen.

7. An apparatus according to claim 1 including
shakers and agitators connected with said mixing mechanism for shaking said mixing mechanism and agitating said infected components and organic agents therein, to facilitate efficient mixing and treating.

8. An apparatus according to claim 1 in which
said measuring mechanism for measuring the residues of said organic agents is a gas chromatograph with automatic sampling.

9. An apparatus according to claim 1 in which
said removal mechanism for substantially removing, denaturing, or neutralizing said organic agents after the completion of said treatment is a system selected from the group consisting of centrifugal systems, distillation systems, vacuum pumps, heating elements, cooling mechanims, compressors, and collectors.

10. An apparatus according to claim 1 including
temperature control mechanisms connected with said mixing mechanism, said removal mechanism, and said measuring mechanism whereby the process of mixing and treating said infected blood components with said organic agents; the process of removing said organic agents from the treated components; and the process of measuring said residues of said organic agents after the treatment is completed, are conducted and maintained at temperatures below 56° C.

11. An apparatus according to claim 1 including
vapor-recovering and condensing mechanisms connected with said removal mechanism for recovering and condensing the removed vapors of said organic agents, after the completion of treatment.

12. An apparatus according to claim 1 in which
said component separators for separating said infected blood substantially into said infected components and substantially healthy or un-infected components is a system selected from the group consisting of centrifugal separator systems and filter systems.

13. An apparatus according to claim 1 including
a mechanism connected with said component separators for substantially separating granulocytes from said infected white cell components; and
a mechanism for returning said granulocytes to said patient.

14. An apparatus according to claim 1 including
a mechanism connected with said second return mechanism for discarding said infected white cells.

15. A method of extracorporeal treatment for viral infections of blood including HIV (Human Immunodeficiency Virus) infections and AIDS caused by enveloped viruses having a lipid envelope and spikes covered by glycoproteins, said method comprises:
  (a) withdrawing blood from an infected patient;
  (b) separating said blood into substantially uninfected components including red cells and platelets, and substantially infected components including plasma and white cells;
  (c) utilizing said uninfected red cells and platelets for transfusion to said patient or a different patient;
  (d) mixing and treating, together or separately, said infected components including plasma and white cells with organic agents in liquid form selected from the group consisting of ethers, halogenated ethers, halogenated hydrocarbons, chlorinated hydrocarbons, acetone, and chloroform, in an amount and over a period of time sufficient to dissolve the envelope and destroy the glycoprotein covered spikes of said viruses (cell-free virus) thereby depriving said viruses of means for penetrating and infecting healthy cells, thus inactivating said viruses; or in an amount and over a period of time sufficient to kill said infected white cells containing virus (replicating virus) thereby stopping the maturation of the virus within said infected white cells without damaging the biochemical constituents of plasma including antibodies, complement, clotting factors, enzymes, and blood factors;
  said amount of organic agents being otherwise too harmful or too toxic to be administered directly to said patient in effective or therapeutic amounts calculated based on the kilograms of body weight or based on the volume of blood;
  (e) after the completion of said mixing and treating of said infected components with said organic agents, substantially neutralizing, denaturing, or separating and removing said organic agents from the treated components, at temperatures below approximately 56° C.;
  (f) measuring the residues of said organic agents in said treated components, after removal of said organic agents, to determine whether said residues are within an acceptable safe range and repeating step (e) as necessary to insure that said treated components are safe for reuse; and thereafter
  (g) utilizing said treated components, together or separately, for transfusion to said patient or a different patient.

16. A method of treatment according to claim 15 in which
said halogenated ethers include: methoxyflurane (2,2-dichloro-1,1-difluoroethyl methyl ether, Penthrane); enflurane (2-chloro-1,1,2-trifluoromethyl difluoromethyl ether, Ethrane); isoflurane (1-chloro-2,2,2-trifluoroethyl difluoroethyl ether, Forane); and fluroxene (2,2,2-triffluoroethyl vinyl ether).

17. A method of treatment according to claim 15 in which
said halogenated hydrocarbons include: halothane (2-bromo-2-chloro-1,1,1-trifluoroethane, Fluothane); trichloroethylene; dichloromethane (methylene chloride); ethyl chloride; ethylene; 1,1,1-trichloroethane; and xylene.

18. A method of treatment according to claim 15 in which
said ethers consist substantially of diethyl ether.

19. A method of treatment according to claim 15 in which
said ethers are selected from the group consisting of ethyl vinyl ether, methyl ether, and propyl ether.

20. A method of treatment according to claim 15 in which
said steps of utilizing said uninfected components and said treated components for transfusion to said patient or a different patient include
storing said uninfected components and said treated components in a blood bank or other suitable environment to be used for subsequent transfusion to said patient or a different patient.

21. A method of treatment according to claim 15 in which
said steps of utilizing said uninfected components and said treated components for transfusion to said patient or a different patient include
combining said treated components with said uninfected components to substantially reconstitute whole blood, and
storing said substantially reconstituted whole blood in a blood bank or other suitable environment for subsequent transfusion to said patient or a different patient.

22. A method of treatment according to claim 15 in which
the extracorporeal flow of blood, or components thereof is continuous during the administration of steps (a) through (f).

23. A method of treatment according to claim 15 including the steps of
after separating said blood into substantially uninfected components and substantially infected components,
separating the infected white cells from the plasma, discarding the infected white cells, and thereafter
carrying out steps (c) through (g) on said infected plasma.

24. A method of treatment according to claim 15 including the steps of;
prior to treating said infected white cells with said organic agents,
separating the granulocytes from said white cells and returning said granulocytes to said patient or a different patient.

25. A method of treatment according to claim 15 in which
said infected white cells include T-4 helper lymphocytes, infected monocytes, and infected macrophages.

26. A method of treatment according to claim 15 including the step of
adding anticoagulants and intravenous fluids to said blood or said components, as needed, during the course of treatment.

27. A method of treatment according to claim 15 in which
said viruses include HTLV-I, HTLV-II, and hepatitus type B viruses.

28. A method of treating units or bags of blood, or components thereof donated by blood donors to prevent the spread of viral infections of blood in recipients including HIV (Human Immunodeficiency Virus) infections and AIDS caused by enveloped viruses having a lipid envelope and spikes covered by glycoproteins, said method comprises:
(a) separating donated blood ,contained in units or bags into substantially uninfected components including red cells and platelets, and substantially infected components including plasma and white cells;
(b) utilizing said uninfected red cells and platelets for transfusion to a recipient;
(c) mixing and treating, together or separately, said infected components including plasma and white cells with organic agents in liquid form selected from the group consisting of ethers, halogenated ethers, halogenated hydrocarbons, chlorinated hydrocarbons, acetone, and chloroform, in an amount and over a period of time sufficient to dissolve the envelope and destroy the glycoprotein covered spikes of said viruses (cell-free virus) thereby depriving said viruses of means for penetrating and infecting healthy cells, thus inactivating said viruses; or in an amount and over a period of time sufficient to kill said infected white cells containing virus (replicating virus) thereby stopping the maturation of the virus within said infected white cells without damaging the biochemical constituents of plasma including antibodies, complement, clotting factors, emzymes, and blood factors;
d) after the completion of said mixing and treating of said infected components with said organic agents, substantially neutralizing, denaturing, or separating and removing said organic agents from the treated components, at temperatures below approximately 56° C.;
(e) measuring the residues of said organic agents in said treated components, after removal of said organic agents, to determine whether said residues are within an acceptable safe range and repeating step (d) as necessary to insure that said treated components are safe for reuse; and thereafter
(f) utilizing said treated components, together or separately, for transfusion to said recipient or a different recipient.

* * * * *